US006514480B1

(12) United States Patent
Sixt

(10) Patent No.: US 6,514,480 B1
(45) Date of Patent: Feb. 4, 2003

(54) METHOD FOR PRODUCING CONTRAST AGENTS LARGELY FREE OF SIDE-EFFECTS

(75) Inventor: Bernhard Sixt, Oberpframmern (DE)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/485,983
(22) PCT Filed: Aug. 20, 1998
(86) PCT No.: PCT/EP98/05305
§ 371 (c)(1),
(2), (4) Date: Apr. 28, 2000
(87) PCT Pub. No.: WO99/10015
PCT Pub. Date: Mar. 4, 1999

(30) Foreign Application Priority Data

Aug. 21, 1997 (DE) .......................... 197 36 472

(51) Int. Cl.$^7$ .......................... A61B 5/055; A61K 49/00
(52) U.S. Cl. .......................... 424/9.3; 424/9.4; 424/9.1
(58) Field of Search ................................ 424/9.4, 9.44, 424/9.411, 9.3, 9.1

(56) References Cited

U.S. PATENT DOCUMENTS 5,204,005 A * 4/1993 Doran, III .................... 210/656
5,779,905 A * 7/1998 Morandi et al. ............ 210/651

FOREIGN PATENT DOCUMENTS

WO    WO-94/14478    *   7/1994   .......... A61K/49/04

* cited by examiner

Primary Examiner—Michael G. Hartley
(74) Attorney, Agent, or Firm—Royal N. Ronning, Jr.; Robert F. Chisholm

(57) ABSTRACT

To lessen the allergic or pseudoallergic side effects of radiological contrast agents, the contrast agent is preincubated in vitro with a reactive medium such as human or animal blood protein, whereupon the resultant reaction products are separated off from the contrast agent by ultrafiltration.

5 Claims, No Drawings

METHOD FOR PRODUCING CONTRAST AGENTS LARGELY FREE OF SIDE-EFFECTS

This application is a 371 of PCT/EP98/05305, filed Aug. 20, 1998.

The invention relates to a method for producing contrast agents largely free side-effects, in particular nonionic, monomeric or dimeric radiological contrast agents, in which the contrast agent is put into contact with a reactive medium having molecules larger than in the contrast agent, so that reactive contaminants contained in the contrast agent from the production process react with the reactive medium, and the reaction products, which are distinguished from the contrast agent by their molecular size, are separated off from the contrast agent.

Such methods, in which contrast agent is cleaned with activated charcoal as a reactive medium or with the aid of ionic exchangers, are known.

Contrast agents are introduced purposefully into the human body, for instance by injection into the bloodstream, in order to make certain parts of the body or the blood flow visible by means of X-rays, which in radioscopy are attenuated especially markedly by the contrast agent. After performing this function, the contrast agent remains in the body and is gradually excreted again via the applicable organs. Hence there is intensive body contact, with the risk of undesired side-effects. In the human being, allergic and pseudoallergic reactions, which can occur spontaneously or after some time, have been observed as a consequence of the administration of contrast agents. Nor can these reactions be substantially lessened by cleaning the contrast agents in a known way.

Earlier, ionic substances (salts) such as iodides, which have two osmotically active particles per iodine molecule, were employed as contrast agents. Later on, nonionic monomeric contrast agents have come onto the market, which contain three iodine atoms covalently on a benzene ring as the basic skeleton, and whose water solubility is attained by means of a plurality of OH groups on side chains. As a result of this arrangement, three iodine molecules are present per osmotically active particle. The most recent development, known as dimeric nonionic contrast agents, are created in principle by the linkage of two nonionic monomeric basic skeletons, and thus they double the number of iodine atoms per osmotically active particle to six. Although the side effects for the nonionic contrast agents compared with the ionic contrast agents have dropped markedly, nevertheless when these substances are administered, side effects and late reactions of an allergic and pseudoallergic nature must be expected, which in rare cases can be so severe as to cause the death of the patient. In the case of nonionic dimeric contrast agents in particular, a trend to pseudoallergic late reactions has been observed. It would therefore be medically relevant to reduce side effects for all radiological contrast agents.

For the present invention, it is significant that allergic reactions are not tripped directly by the contrast agent, since its molecules are much too small to be detected by the body as an allergen. The allergenic effect thus comes into play only once a contrast agent molecule has bonded to a larger molecule, such as an albumin molecule. Pseudoallergic reactions, whose triggers and mechanism are still unexplained at present, are also more likely tripped by a small quantity of reactive contaminant or contaminants than by the contrast agent itself. If the contrast agent caused these reactions, then quantities of up to 300 ml and more should lead to far greater rates of side effects. It should be remembered that injecting 300 ml of a contrast agent available on the market, with a purity of 99.5%, at the same time means the administration of a quantity of 1.5 ml of unknown contaminants. It can therefore be assumed that the substances that trip the undesired reactions are not the contrast agent itself, but rather slight traces present in it of contaminants, which occur in the synthesis of the contrast agent and as is known cannot be removed absolutely completely even with careful cleaning.

This is the point of departure for the invention. It is based on the concept of performing the reaction, which previously took place in the body, outside the body beforehand instead, and separating off the reaction products that occur from the contrast agent before the contrast agent is used. This means cleaning of the contrast agent by preincubation.

Accordingly, the method of the invention is characterized in that substances of human, animal or vegetable origin are used as the reactive medium.

Thus according to the invention, in vitro preincubation is performed, which makes for markedly enhanced tolerance of the thus-treated and separated contrast agent.

Expedient provisions in performing the method of the invention are recited in the dependent claims. Accordingly, as reactive substances, proteins or albumins of human, animal or vegetable origin and in particular blood proteins or blood, and specifically including human blood, can be used, which to a marked extent simulates the conditions and processes that until now occurred in the body when contrast agents were administered.

EXAMPLE

After synthesis, the contrast agent is put into contact with a reactive medium, in order to allow the reactive contaminants to react. Whole human blood is used as the reactive medium, in order to identically simulate the conditions in the body as much as possible. The reactive medium is incubated with the contrast agent at an elevated temperature, for instance 37 C. Next, the resultant reaction product is separated off, together with the unconsumed reactive medium; this can economically be done simply by ultrafiltration, which can be performed simultaneously with the final production step.

As an alternative to ultrafiltration, in the case of an insoluble reactive medium, the contrast agent can simply be passed through a granulate layer of the reactive medium. Other reactive mediums can also be employed if they are bound to an inner vehicle material.

Although whole human blood contains all the possible reaction partners with which the contrast agent comes into contact in the body when administered, and moreover all the medically questionable components of human blood are removed again by the ultrafiltration or separation off of the contrast agent treated according to the invention, it is advantageous from both a medical and a financial standpoint to identify the actual reaction partners in the blood and to employ them in cleaned form for the preincubation. The procedure can be as follows:

By incubating radioactively labeled radiological contrast agent with whole blood, followed by repeated washing using ultrafiltration, a protein residue is obtained, which is analyzed; the now-radioactive product is identified by electrophoresis, and as a result the reaction partner with which the contrast agent can be cleaned in a targeted way is determined.

The method of the invention is not limited to the radiological contrast agent addressed above primarily; on the contrary, other contrast agents, such as magnetic resonance contrast agents, can be preincubated in vitro and cleaned as described above, thereby improving their tolerance. Contrast agents that one skilled in the art can consider using are also known—for instance on the basis of the information provided in International Patent Application WO 97/30735.

What is claimed is:

1. A method for producing contrast agents largely free of side effects, comprising the steps of:

a) placing a contrast agent into contact with a reactive medium selected from the group consisting of human or animal blood or blood proteins, said reactive medium having molecules larger than in the contrast agent so that the reactive contaminants contained in the contrast agent react with the reactive medium to form reaction products; and b) separating off the reaction products from the contrast agent, wherein the reaction products and the contrast agent have different molecular sizes.

2. The method according to claim 1, wherein the contrast agents are selected from the group consisting of magnetic contrast agents and radiological contrast agents.

3. The method according to claim 2, wherein the radiological contrast agents are selected from the group consisting of nonionic, monomeric, and dimeric radiological contrast agents.

4. The method according to claim 1, wherein step a) is carried out at a temperature in the range of 35° to 40° C.

5. The method according to claim 1, wherein step b) is done by ultrafiltration.

* * * * *